US010881791B2

(12) United States Patent
Wolff

(10) Patent No.: US 10,881,791 B2
(45) Date of Patent: Jan. 5, 2021

(54) INFUSION DEVICE AND METHOD FOR ADMINISTERING A MEDICAL FLUID TO A PATIENT

(71) Applicant: Fresenius Vial SAS, Brézins (FR)

(72) Inventor: Rémy Wolff, Morette (FR)

(73) Assignee: Fresenius Vial SAS, Brézins (FR)

(*) Notice: Subject to any disclaimer, the term of this patent is extended or adjusted under 35 U.S.C. 154(b) by 164 days.

(21) Appl. No.: 16/083,319

(22) PCT Filed: Mar. 10, 2017

(86) PCT No.: PCT/EP2017/055673
§ 371 (c)(1),
(2) Date: Sep. 7, 2018

(87) PCT Pub. No.: WO2017/162447
PCT Pub. Date: Sep. 28, 2017

(65) Prior Publication Data
US 2019/0070359 A1 Mar. 7, 2019

(30) Foreign Application Priority Data
Mar. 23, 2016 (EP) .................................. 16305327

(51) Int. Cl.
A61M 5/14 (2006.01)
A61M 5/168 (2006.01)
A61M 5/145 (2006.01)

(52) U.S. Cl.
CPC ...... A61M 5/16854 (2013.01); A61M 5/1456 (2013.01); A61M 2005/16863 (2013.01); A61M 2205/18 (2013.01); A61M 2205/332 (2013.01)

(58) Field of Classification Search
CPC ............ A61M 5/16854; A61M 5/1456; A61M 2205/332; A61M 2205/18; A61M 2005/16863
See application file for complete search history.

(56) References Cited

U.S. PATENT DOCUMENTS

| 5,242,408 A | 9/1993 | Jhuboo et al. |
| 2004/0133166 A1 | 7/2004 | Moberg et al. |

(Continued)

FOREIGN PATENT DOCUMENTS

| CN | 1942210 | 4/2007 |
| CN | 101371127 | 2/2009 |

(Continued)

OTHER PUBLICATIONS

International Search Report and Written Opinion, counterpart International Appl. No. PCT/EP2017/055673, dated Jun. 28, 2017 (19 pages).

(Continued)

Primary Examiner — Amber R Stiles
(74) Attorney, Agent, or Firm — Cook Alex Ltd.

(57) ABSTRACT

An Infusion device (1) for administering a medical fluid to a patient (P), comprises: a receptacle (12) for receiving a syringe (2) having a tube (20) containing a medical fluid and a piston (21) movable with respect to the tube (20); a pusher device (11) for acting onto the piston (21) for pumping the medical fluid from the tube (20) towards a patient (P) at a set flow rate; a sensor device (14) for measuring a force acting in between the pusher device (11) and the piston (21) of the syringe (2); and a processor device (15) for deriving, from the force measured by the sensor device (14), a pressure value indicative of the pressure in the delivery line (3), wherein the processor device (15) is constituted to compare the pressure value to a threshold value ($P_{thres}$) for determining whether an occlusion (O) in the delivery line (3) is present. Herein, the processor device (15) is constituted to determine the threshold value ($P_{thres}$) from a first threshold value candidate computed based on a desired time between the time (t0) of an occurrence of an occlusion (O) in the delivery line (3) and the time (t1) at which the pressure value (Continued)

exceeds the threshold value ($P_{thres}$), and a second threshold value candidate based on a force error estimate of a possible deviation between an expected frictional force and a true frictional force occurring when moving the piston (21) relative to the tube (20).

13 Claims, 3 Drawing Sheets

(56) References Cited

U.S. PATENT DOCUMENTS

| | | |
|---|---|---|
| 2007/0270747 A1 | 11/2007 | Remde |
| 2009/0118667 A1 | 5/2009 | Haueter et al. |
| 2012/0283691 A1 | 11/2012 | Barnes et al. |
| 2014/0058351 A1 | 2/2014 | Pope et al. |
| 2014/0121632 A1* | 5/2014 | Haenggi ............. A61M 5/1456 604/500 |

FOREIGN PATENT DOCUMENTS

| | | |
|---|---|---|
| JP | 2001-245978 A | 9/2001 |
| WO | WO2013/004308 A1 | 1/2013 |
| WO | WO2014/072195 A1 | 5/2014 |

OTHER PUBLICATIONS

Search Report, counterpart Chinese App. No. 201780018828.1 (dated Jul. 23, 2020) (2 pages).
First Office Action with English translation, counterpart Chinese App. No. 201780018828.1 (dated Jul. 29, 2020) (15 pages).

* cited by examiner

INFUSION DEVICE AND METHOD FOR ADMINISTERING A MEDICAL FLUID TO A PATIENT

The present application is a U.S. National Stage of PCT International Patent Application No. PCT/EP2017/055673, filed Mar. 10, 2017, which claims priority to EP Application No. 16305327, filed Mar. 23, 2016, both of which are hereby incorporated herein by reference.

The invention relates to an infusion device for administering a medical fluid to a patient according to the preamble of claim 1 and to a method for administering a medical fluid to a patient.

An infusion device of this kind comprises a receptacle for receiving a syringe having a tube containing a medical fluid and a piston movable with respect to the tube. A pusher device is constituted to act onto the piston for pumping the medical fluid from the tube towards a patient. During infusion, a sensor device measures a force acting in between the pusher device and the piston of the syringe, and a processor device derives, from the force measured by the sensor device, a pressure value indicative of the pressure in the tube, wherein the processor device is constituted to compare the pressure value to a threshold value for determining whether an occlusion in a delivery line connected to the tube is present.

Within a syringe pump, a medical fluid (such as a medication or a nutritional fluid for example for the parenteral feeding of a patient) is contained in a cylindrical tube of a syringe. By continuously pushing a piston of the syringe into the cylindrical tube the medical fluid is delivered out of the cylindrical tube through a suitable delivery line towards a patient for infusing the medical fluid into the patient.

Within a syringe pump, a force sensor is for example placed on a driving element of the pumping mechanism of the infusion device acting onto the piston of the syringe. By measuring the force exerted on the piston the pressure within the cylindrical tube of the syringe (which is connected downstream to the delivery line) can be derived.

Generally herein, the pressure within the cylindrical tube during a normal infusion process can be assumed to be (almost) 0, due to the resistance for delivering the medical fluid towards the patient being small. However, if an occlusion is present in the delivery line downstream of the cylindrical tube of the syringe, the pressure in the cylindrical tube will rise, which can be detected via the force sensor and which can be used to trigger an alarm if the pressure exceeds a certain preset threshold value.

The pressure threshold value used for the occlusion detection is conventionally for example programmed by a user prior to conducting an infusion operation. Herein the user may enter a desired threshold value during the initial programming of the device, and this threshold value is then used during operation for detecting whether an occlusion is present or not.

In this regard, however, the user must be aware of the fact that generally an alarm will not be triggered immediately upon occurrence of an occlusion. Rather, the pressure measured on the pumping mechanism or on the delivery line will rise continuously and will reach the threshold value only some time after the actual occurrence of the occlusion. The time between reaching the threshold and the actual occurrence of the occlusion depends for example on the flow rate, the set threshold value and the mechanical characteristics of the pumping mechanism or the tubing set used together with the pumping mechanism. An alarm hence is triggered only after a substantial time has passed following the occurrence of an occlusion, for example 30 minutes, an hour or even more after the occlusion first occurred. If a continuous infusion of a medical fluid into a patient at a constant dose rate is required, a prolonged interruption of the infusion process may pose a severe problem and potentially may be hazardous to the patient.

Generally, in the instructions for use distributed with an infusion device it is stated, for example in a table, what time may pass between the occurrence of an occlusion and the actual triggering of an alarm. This approach however has drawbacks, because a user generally will not refer to the instructions for use prior to each infusion operation, and the instructions for use generally will list estimated time delays only for certain situations, for example for specific tubing sets at specific flowrates, but cannot cover all different scenarios and may not allow a user to easily derive an estimate for a specific situation not explicitly included in the description.

A user, for example a nurse, hence may have a rather low confidence in the triggering of an occlusion alarm, which may cause the user to check on the infusion device more often than actually necessary, putting an additional burden on the user, for example a nurse, which already is faced with a great variety of different tasks for example in a hospital environment, for example in an intensive care unit of a hospital.

Generally, it is a desire to set the threshold value as low as possible such that an occlusion can be detected quickly and an alarm can be triggered soon after the actual occurrence of the occlusion. However, setting a low threshold value may come with the drawback that the risk for false alarms is significantly raised.

The problem of finding a suitable threshold value is furthermore made more complex because syringes of different models, types and volumes and even syringes of the same type and model may have a different frictional behavior such that a threshold for one syringe may not be suitable for another syringe.

It is an object of the instant invention to provide an infusion device and a method for administering a medical fluid to a patient which may facilitate the determination of a threshold value for the occlusion detection and may provide a higher level of confidence to a user for the occlusion detection.

This object is achieved by means of an infusion device comprising the features of claim 1.

Accordingly, the processor device is constituted to determine the threshold value from
 first threshold value candidate computed based on a desired time between the time of an occurrence of an occlusion in the delivery line and the time at which the pressure value exceeds the threshold value, and
 a second threshold value candidate based on a force error estimate of a possible deviation between an expected frictional force and a true frictional force occurring when moving the piston relative to the tube.

In this way, the threshold value used for the occlusion detection shall be optimized. This shall take place based on two criteria.

The first criteria herein shall provide for a fast occlusion detection. For this, a first threshold value candidate is computed based on a desired time which lapses between the actual occurrence of the occlusion and the moment at which the pressure value exceeds the threshold value. The desired time hence indicates the time which lapses between the actual occurrence of the occlusion and the triggering of an alarm. The desired time may be programmed by a user, for example a nurse, when configuring the infusion device for performing an infusion operation. The desired time may, however, also be pre-programmed such that a default value for the desired time for example a time between 1 and 10 minutes, for example 2 minutes, is used as the desired time unless a user programs another value for the desired time.

By computing the first threshold value candidate using the desired time a (low) candidate value for the pressure threshold is obtained which may provide for a fast occlusion detection.

However, the first threshold value candidate computed from the desired time is not used per se as threshold value, but a second threshold value candidate is additionally computed and taken into account as a second criteria, this second criteria being chosen such that the likelihood for false alarms is kept small. Hence, the second criteria is chosen such that the setting of too low a pressure threshold is avoided, at the expense of a (slightly) longer time which may lapse between the actual occurrence of the occlusion and the triggering of an alarm (when the pressure exceeds the threshold value).

The second threshold value candidate is computed based on a force error estimate of a possible deviation between an expected frictional force and a true frictional force occurring when moving the piston relative to the tube. Generally, the pressure value indicative of the pressure in the delivery line may for example be determined according to the following equation:

$$P = \frac{F - F_0}{S}.$$

Herein, P represents the pressure, F represents the measured force and $F_0$ represents a frictional force component. S represents the effective cross sectional surface of the tube (defined by its diameter). Generally, the measured force F is known from the sensor reading measuring the force in between the pusher device and the piston of the syringe. Also, the effective surface S is known from the geometry of the syringe used. However, the frictional force component $F_0$ generally is subject to uncertainty.

The frictional force component, namely the frictional force that in particular arises in between the piston and the tube when moving the piston of the syringe relative to the tube, may in particular differ between different syringes of different types, models and volumes and even between different syringes of the same type, model and the volume.

Generally, to derive the pressure value P, the frictional force component is estimated, for example from a statistical analysis of different syringes of different types, models and volumes prior to conducting an actual infusion operation (this for example may be done by the manufacturer of the infusion device). Also, it is possible to model the behavior of the frictional force for different syringes of different types, models and volumes.

When computing the pressure value for detection of an occlusion, the frictional force component hence is estimated and is taken into account for deriving the pressure value. Generally, if no occlusion is present in the delivery line, it can be assumed that the pressure within the delivery line is (almost) 0, such that the frictional force component is comparable to the measured force. If there is an occlusion in the delivery line, however, the measured force will rise, and likewise the pressure value will rise. Hence, if the pressure value exceeds the set threshold value, it is concluded that an occlusion may be present and an alarm is triggered.

Because the frictional force component is subject to uncertainty and may differ between different syringes of different types, models and volumes and even between different syringes of the same type, model and volume, there may be a deviation between an expected frictional force (determined for example from statistical analysis by measuring the frictional behavior of different syringes) and the true frictional force occurring for the particular syringe used for the infusion. Because of this deviation, the pressure value derived from the above equation may not be fully accurate, such that the occlusion detection performed by comparing the derived pressure value with the threshold value may not be fully precise and in particular may cause false alarms if the actual frictional force occurring when moving the piston relative to the tube is for example smaller than the expected frictional force.

Hence, within the second criteria used to determine the threshold value a possible deviation between the true frictional force occurring when moving the piston relative to the tube and an expected frictional force is taken into account, this possible deviation being expressed as a force error estimate which indicates a possible deviating friction (as compared to an expected friction) when moving the piston relative to the tube.

In one aspect, the threshold value may be set to be the maximum of the first threshold value candidate and the second threshold value candidate. Hence, the maximum of the two computed candidates is chosen as the threshold value, hence ensuring that a comparatively short time between the actual occurrence of the occlusion and the actual triggering of an alarm is obtained, but at the same time ensuring that the likelihood for false alarms is kept small.

The infusion device may for example comprise a storage device storing a compliance value associated with the syringe and/or the delivery line connected to the tube of the syringe. The processor device herein is constituted to compute the first threshold value candidate from the stored compliance value, a set flow rate and the desired time. In particular, the processor device may be constituted to compute the first threshold value candidate according to the following equation:

$$P_{thres,1}[\text{bar}] = \frac{T_{desired}[\text{h}] \cdot f[\text{ml/h}]}{C[\text{ml/bar}]}$$

Herein, $P_{thres,1}$ represents the first threshold value candidate (in bar), $T_{desired}$ represents the desired time (in hours) between the time of an occurrence of an occlusion in the delivery line and the time at which the pressure value exceeds the threshold value, C represents the compliance value (in ml/bar), and f represents the flow rate (in ml/h).

In one aspect, the storage device may store a multiplicity of compliance values associated with a multiplicity of different syringes and/or delivery lines. This is based on the finding that different syringes and different delivery lines generally have different compliances, depending on the structural built of the syringe and the delivery line and the materials used, for example. By storing different compliance values for different syringes and different delivery lines, when using a particular syringe and a particular delivery line the associated compliance value may be chosen and the first threshold value candidate may be determined accordingly.

The compliance value in this regard is to be understood as a measure for the expansibility of the system, for example a cylindrical tube of a syringe used on the syringe pump or a delivery line extending between the pumping mechanism and the patient. Generally, the compliance indicates the change of volume per pressure and accordingly is stated for example in ml/bar. With respect to for example a tubing set, the compliance indicates by what volume a tube expands if the pressure increases by a certain margin.

The compliance for a system can be measured easily by subjecting a system, for example a tube set, to pressure and measure the change in volume.

The instant invention makes use of the finding that the rise of pressure within the system also depends on the compliance of the system. A large compliance will lead to a slower rise in pressure (because the system, for example a tubing set, expands when the pressure rises), whereas a small compliance will lead to a fast rise in pressure.

If a particular type of syringe is not defined within the storage device, for example a default value may be used. If for example a syringe is used of a particular manufacturer having a predefined volume, for example 50 ml, a default value for a 50 ml syringe may be used if the particular syringe from the particular manufacturer is not known to the system.

The compliance value may be a constant or may be defined by a (non-linear) relation depending on the pressure.

Generally, the desired time may be programmed by a user via a suitable input device, for example a touch sensitive screen, of the infusion device. Likewise, the flow rate may be programmed by a user prior to starting the infusion process.

It however is also conceivable that the desired time is pre-programmed within the system such that a default value for the desired time is used unless the desired time is programmed differently by a user upon starting an infusion operation.

For determining the second threshold value candidate, the storage device may store, for at least one particular syringe type, a mean frictional force required to move the piston relative to the tube and a standard deviation of the mean frictional force. The processor device, in this case, may be constituted to determine the force error estimate used to compute the second threshold value candidate using the standard deviation for a syringe of a particular syringe type, for example by multiplying the standard deviation by a constant factor. Hence, the storage device holds, for a particular syringe, a mean frictional force and a standard deviation for this mean frictional force. The mean frictional force is used to derive the pressure value for comparing it to the threshold value, as explained above. The standard deviation, in turn, is used to compute the force error estimate in order to obtain the second threshold value candidate, for example by multiplying the standard deviation by a constant factor, for example in the range between 1 and 4, for example 2.

The stored mean frictional force and/or the stored standard deviation may, in one aspect, be dependent on the position of the piston relative to the tube. This is based on the finding that the friction occurring between the piston and the tube may vary as the piston is moved within the tube. By storing position dependent mean frictional force values for a particular syringe and also position dependent standard deviation values for the particular syringe, hence, the frictional behavior may be modeled as a function of the position.

In addition, the mean frictional force and/or the start standard deviation may vary as a function of the speed by which the piston is moved relative to the tube. Hence, the storage device may also hold different mean frictional force values and/or standard deviation values for different speeds of moving the piston relative to the tube.

The mean frictional force of a particular syringe may for example be obtained by measuring the frictional force when moving the piston relative to the tube in calibration tests prior to the actual infusion operation (such tests may for example be performed by the manufacturer of the device). The mean frictional force, and also the standard deviation, herein may be obtained by statistical analysis. As said, the mean frictional force and the standard deviation may be position dependent and also speed dependent.

Alternatively, the force error estimate may be determined from the mean frictional force alone stored in the storage device. For example, the force error estimate may be obtained by multiplying the mean frictional force by a constant factor, for example in the range between 1 and 3, for example 1.5. Again, the mean frictional force stored in the storage device may be dependent on the position of the piston relative to the tube and/or the speed by which the piston is moved relative to the tube.

In another alternative, the force error estimate may be stored directly as a parameter within the storage device. Hence, for different syringes of different types, different force error estimate parameters may be stored within the storage device.

The force error estimate indicates a possible deviation of a true frictional force from an expected frictional force (for example a mean frictional force stored in the system). The force error estimate hence indicates by what margin possibly the frictional force of an actually used syringe may differ from the frictional force component ($F_0$ in the equation above) used to derive the pressure value for comparing it to the threshold value. This force error estimate, as described above, may for example be derived from the standard deviation, or may be stored directly in the system. From the force error estimate, then, the second threshold value candidate may be computed according to the following equation:

$$P_{thres,2}[\text{bar}] = \frac{F_{est}[gf]}{10.2 \cdot S[\text{mm}^2]}$$

Herein, $P_{thres,2}$ represents the second threshold value candidate (in bar), $F_{est}$ represents the force error estimate (in gram force (gf)), and S represents the effective cross sectional surface (in mm²) of the tube, defined as $S=\pi \cdot (D/2)^2$, D being the inner diameter of the cylindrical tube.

The object is also achieved by a method for administering a medical fluid to a patient using an infusion device comprising:
  receiving a syringe having a tube containing a medical fluid and a piston movable with respect to the tube in a receptacle of the infusion device,
  pumping the medical fluid from the tube towards a patient by acting onto the piston using a pusher device,
  measuring a force acting in between the pusher device and the piston of the syringe using a sensor device, and
  deriving, from the force measured by the sensor device, a pressure value indicative of the pressure in the tube of the syringe using a processor device, wherein the pressure value is compared to a threshold value for determining whether an occlusion in a delivery line connected to the tube is present.

The threshold value is determined from
- a first threshold value candidate computed based on a desired time between the time of an occurrence of an occlusion in the delivery line and the time at which the pressure value exceeds the threshold value, and
- a second threshold value candidate computed based on a force error estimate of a possible deviation between an expected frictional force and a true frictional force occurring when moving the piston relative to the tube.

The advantages and advantageous embodiments described above for the infusion device likewise apply also to the method, such that it shall be referred to the above.

The idea of the invention shall subsequently be described in more detail with reference to the embodiments shown in the figures. Herein:

Figure 1:
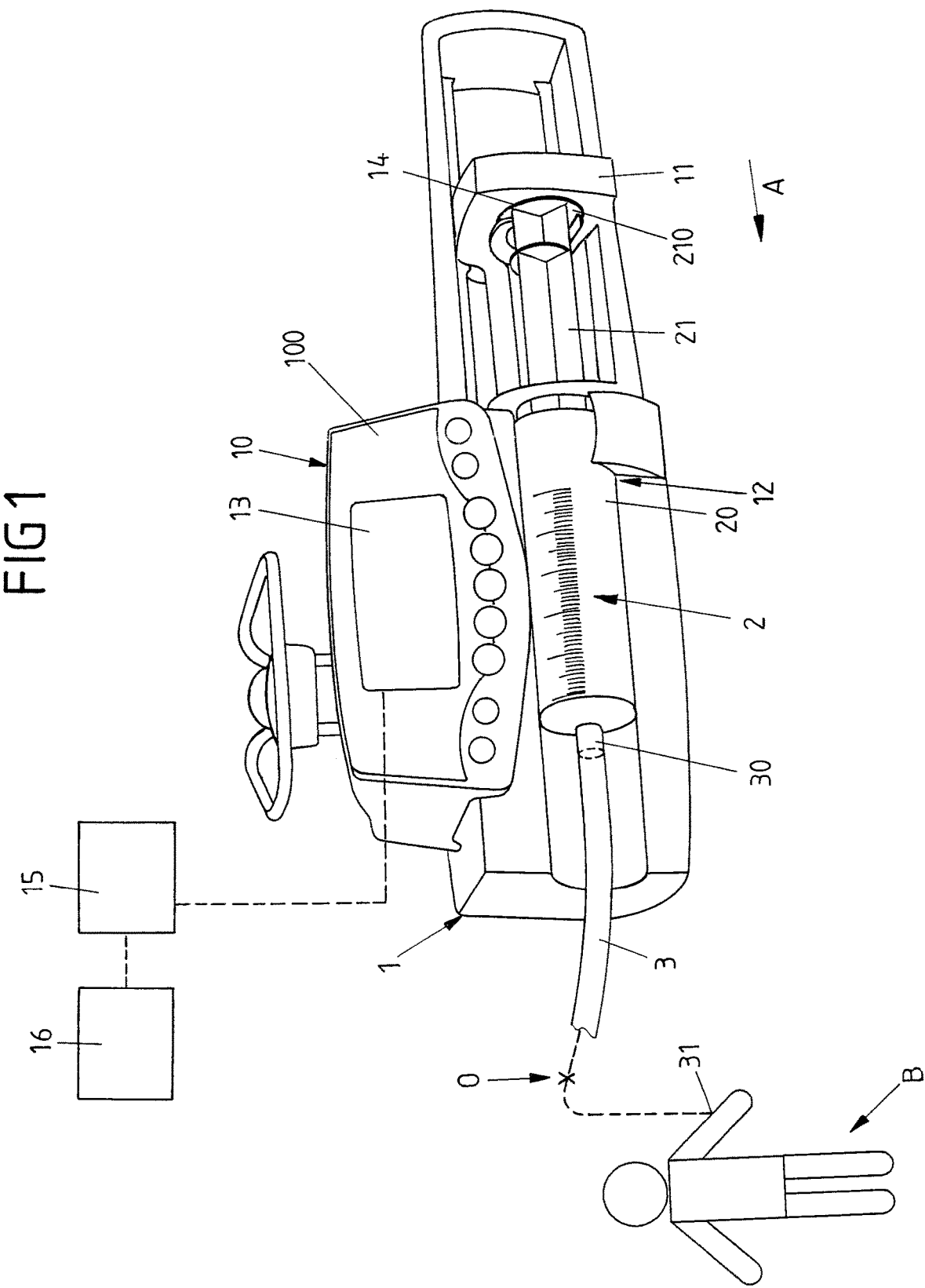
FIG. 1 shows a view of an infusion device constituted as a syringe pump.

FIG. 3A-3D schematic views of different syringes having different characteristics; and FIG. 4A-4D graphical views of the frictional force dependent on the position for the different syringes according to FIG. 3A to 3D;

FIG. 1 shows an embodiment of an infusion device 1 in the shape of a syringe pump. The infusion device 1 comprises a housing 10 having a front face 100 and a display device 13 arranged thereon. The display device 13 may for example be a touch-sensitive display allowing a user to enter commands for operation of the infusion device 1 and displaying operational information regarding the process of an actual infusion operation.

The infusion device 1 comprises a receptacle 12 in which a syringe 2 having a cylindrical tube 20 is arranged. A piston 21 is movable within the cylindrical tube 20 and is in engagement with a pusher device 11 of a pumping mechanism of the infusion device 1. At an end of the cylindrical tube 20 opposite the piston 21 a delivery line 3 extends from the cylindrical tube 20 towards a patient B, the delivery line 3 being connected to the cylindrical tube 20 at an end 30 and to the patient B at an end 31.

The piston 21 comprises a head 210 facing away from the cylindrical tube 20 and being in abutment with the pusher device 11 of the infusion device 1. During operation of the infusion device 1, the pusher device 11 is electromotorically driven in an actuation direction A such that the piston 21 is moved into the cylindrical tube 20 and a medical fluid contained in the cylindrical tube 20 is delivered via the delivery line 3 towards the patient B.

The infusion device 1 comprises a processor device 15 and a storage device 16. Via the processor device 15 the infusion operation of the infusion device 1 is controlled. In the storage device 16 operational parameters, such as mechanical characteristics of the syringe 2 used on the infusion device 1 as well as operational data, may be stored.

During an infusion process a medical fluid, for example a medication or a nutritional fluid for the parenteral feeding of a patient or the like, is delivered from the cylindrical tube 20 via the delivery line 3 towards the patient B. For this, the piston 21 is continuously pushed into the cylindrical tube 20 in an actuation direction A such that a desired flow rate is obtained, which is programmed by a user prior to the start of the infusion operation.

The delivery line 3 generally is made of a flexible tubing made for example from a PVC material. The delivery line 3 extends from the cylindrical tube 20 to the patient B and is, at its first end 30, in fluid connection with the cylindrical tube 20 and, at its second end 31, for example connected to a needle for providing an intravenous access to the patient B. During an infusion process an occlusion O in the delivery line 3 must be avoided and, if it nevertheless occurs, must be detected such that appropriate countermeasures to overcome the occlusion O can be taken. For this, a force sensor 14 is placed on the pusher device 11 facing the head 210 of the piston 214 measuring a force exerted on the piston 21 during an infusion process. From a force measured by means of the force sensor 14 an estimate of the pressure within the syringe 2 can be obtained, such that the pressure within the syringe 2 and the delivery line 3 can be monitored. If it is found that the pressure within the syringe 2 and the delivery line 3 rises beyond a permissible threshold value, an alarm is triggered indicating that an occlusion O may be present in the system.

Figure 2:
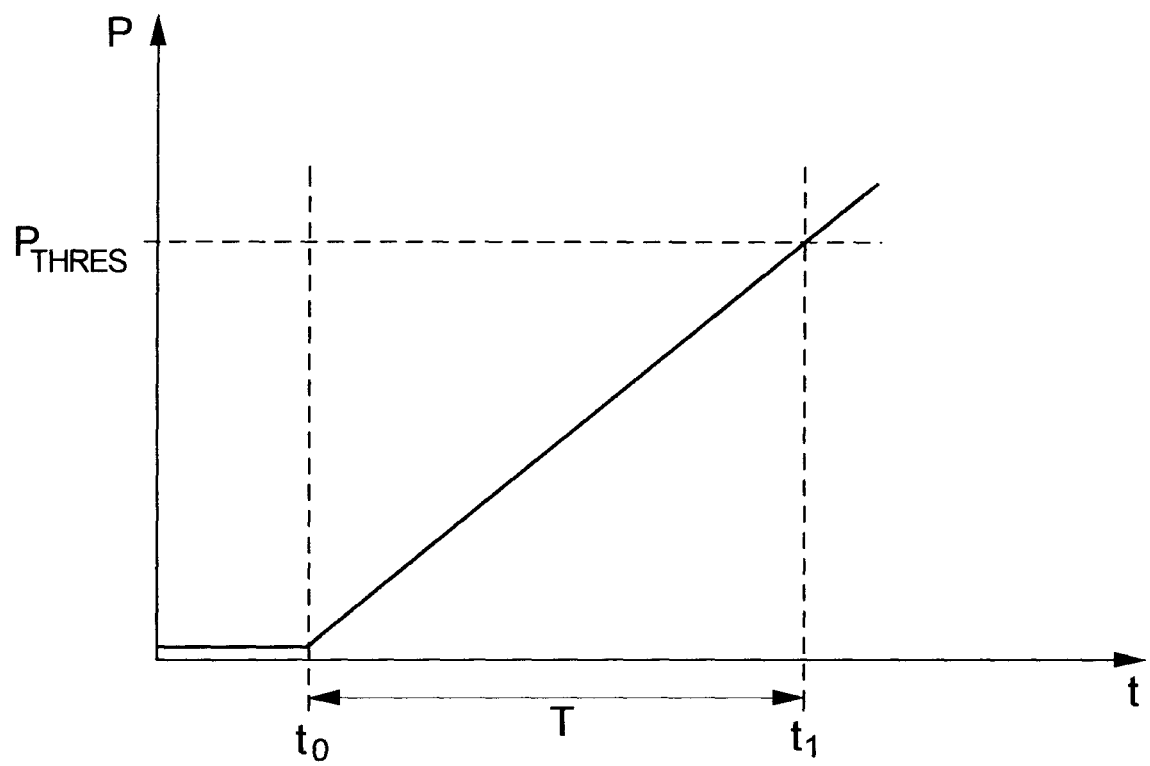
FIG. 2 shows a schematic diagram of a pressure rise over time in case of an occlusion.
Figure 3A:
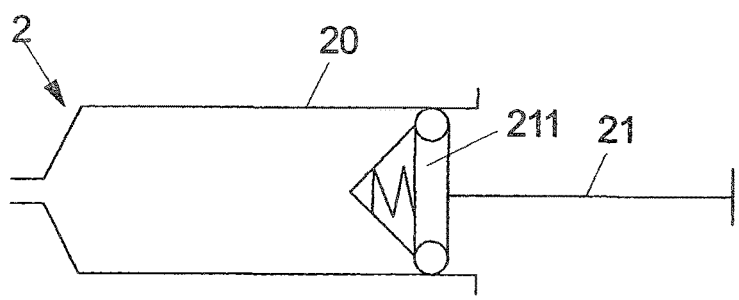
Figure 4A:
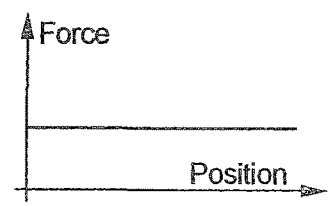
Figure 3B:
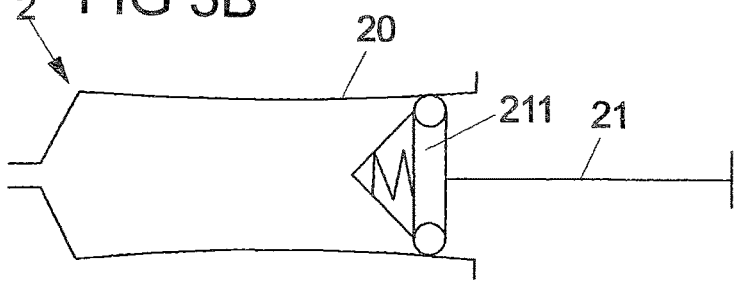
Figure 4B:
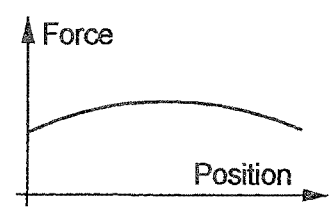
Figure 3C:
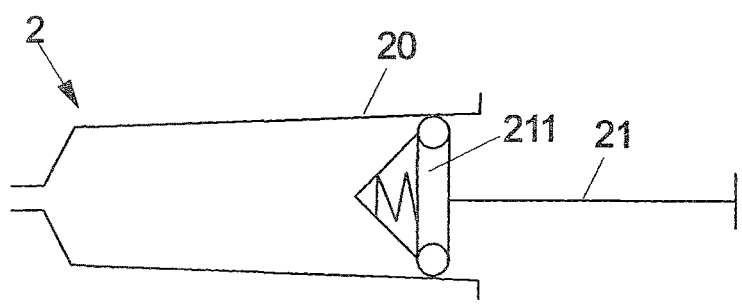
Figure 4C:
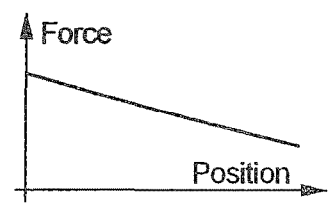
Figure 3D:
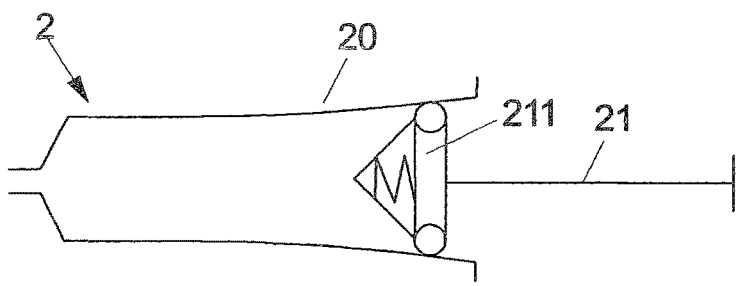
Figure 4D:
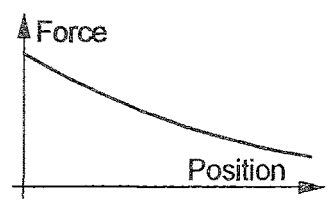

FIG. 2 shows in a schematic diagram the pressure P over time tin case of an occlusion O. Generally, the pressure P is very small (almost 0) during normal infusion operation in case no occlusion O is present (see the pressure P prior to the time t0). If at the time t0 an occlusion O occurs, the pressure P will start to rise and will continue to rise (if the occlusion O does not disappear) until a threshold value $P_{thres}$ is exceeded, at which moment an alarm is triggered by the processor device 15 such that a user is warned of the occlusion O.

The occlusion O, in the example of FIG. 2, occurs at time t0. Until the pressure threshold value $P_{thres}$ actually is exceeded by the pressure curve P at time t1, a substantial time duration T may pass, due to the continuous rise of the pressure P following the occlusion O at a finite slope, the slope of the pressure rise herein depending on a multiplicity of factors, for example the flow rate and the compliance of the system, in particular the compliance of the cylindrical tube 20 of the syringe 2 and of the delivery line 3 extending in between the cylindrical tube 20 and the patient B.

Generally, the pressure in the delivery line 3 will rise according to the following equation:

$$P = \frac{f \cdot t}{C}.$$

Herein, P denotes the pressure, f denotes the flow rate, t denotes the time, and C denotes the compliance.

Making use of the above equation, a threshold value $P_{thres}$ may be determined in order to obtain a fast occlusion detection. Namely, if the compliance C and the flow rate f is known, by assuming a desired time which shall lapse between the actual occurrence of an occlusion and the moment at which the pressure exceeds the pressure threshold value $P_{thres}$ an optimum pressure threshold $P_{thres}$ can be determined, which is low such that a fast occlusion detection may be obtained.

If however the pressure threshold value $P_{thres}$ is chosen too small, false alarms may be triggered, which may hinder the usability of the infusion device 1.

Hence, it is proposed to choose the pressure threshold value $P_{thres}$ according to two criteria, the first criteria taking into account the desired time and the second criteria serving to limit the likelihood for false alarms.

According to the first criteria, a first pressure threshold value candidate can for example be determined according to the following equation:

$$P_{thres,1}[\text{bar}] = \frac{T_{desired}[\text{h}] \cdot f[\text{ml/h}]}{C[\text{ml/bar}]}.$$

Herein, $P_{thres,1}$ represents the first threshold value candidate in bar, $T_{desired}$ represents the desired time (in hours) between the time t0 of an occurrence of an occlusion O in the delivery line 3 and the time t1 at which the pressure value exceeds the threshold value $P_{thres}$, C represents the compliance value (in ml/bar), and f represents the flow rate (in ml/h).

The compliance value C associated with the syringe 2 and the delivery line 3 is stored in the storage device 16 of the infusion device 1. The storage device 16 in this regard may store a multiplicity of compliance values C for different syringes 2 and different delivery lines 3 such that, by inputting for example the type of syringe 2 to the infusion device 1, the processor device 15 may refer to the compliance value C associated with the particular syringe 2 used on the system for computing the estimate of the duration T.

The storage device 16 may for example store a compliance value for a syringe 2 of a particular manufacturer and a particular volume. The storage device 16 may in addition store a default value for a syringe 2 of a particular volume, which may be used in case a particular syringe 2 of a particular manufacturer is not explicitly defined in the infusion device 1. A delivery line 3 may be identified by its length, its inner and/or outer diameter or the like and by its manufacturer, and associated with a particular type of delivery line 3 a particular compliance value may be stored in the storage device 16.

The storage device 16 may store a constant value for the compliance. Just as well it is conceivable that the storage device 6 stores a nonlinear relation for the compliance depending for example on the pressure in the system.

If this first pressure threshold value candidate would be chosen as the pressure threshold value $P_{thres}$, a fast occlusion detection would be obtained. This however would come at the expense of a possibly increased likelihood of a false alarm if the pressure threshold value $P_{thres}$ is chosen too small in this way.

Therefore, a second criteria is applied in addition.

The second criteria is derived based on the following background:

To observe the pressure in the delivery line 3, the force applied to the piston head 210 of the piston 21 by means of the pusher device 11 is measured by a sensor 14 placed in between the pusher device 11 and the piston head 210. The force measured in this way allows for an indirect measurement of the pressure within the cylindrical tube 20, which generally equals the pressure in the delivery line 3.

In particular, the pressure in the cylindrical tube 20 depends on the measured force according to the following relation:

$$P = \frac{F - F_0}{S}.$$

Herein, P denotes the pressure, F denotes the measured force, $F_0$ denotes a frictional force component and S denotes the effective surface by which the piston 21 acts onto the liquid contained in the cylindrical tube 20. The effective surface S is substantially determined by the inner diameter of the cylindrical tube 20.

By determining the pressure P in this way and by comparing the determined pressure P to a predefined threshold $P_{thres}$ it can then be concluded whether an occlusion O is present in the delivery line 3 or not. In particular, if it is found that the pressure P rises above the threshold $P_{thres}$, it is concluded that an occlusion O is present.

Whereas F is measured and S is known from the geometrical dimensions of the cylindrical tube 20 of the syringe 2, the frictional force component $F_0$ cannot be determined in an easy way. In particular, the frictional force component $F_0$ may vary in dependence on the specific syringe 2 used on the system, wherein the frictional force component $F_0$ generally is dependent on the position of the piston 21 within the cylindrical tube 20 and on the velocity by which the piston 21 is moved relative to the cylindrical tube 20 during an infusion process.

The frictional force component $F_0$ depends at least on the following parameters (sorted approximately—by their relevance for the frictional force):
- the syringe brand, model and batch
- the pushing velocity,
- the position of the piston on its full travel range,
- the temperature,
- the waiting time between syringe preparation and infusion start,
- the liquid inside the syringe, and
- the pressure.

It is to be noted that the catheter size, the extension line diameter and length and the drug viscosity generally can be considered to have no influence on the frictional force. But these parameters may of course have an influence on the pressure.

In addition, as visible from FIG. 3A to 3D, the structural characteristics in particular of the cylindrical tube 20 in which a stopper 211 of a piston 21 is moved may vary along the travel range of the piston 21 relative to the cylindrical tube 20. In particular, the cylindrical tube 20 may not exhibit a constant diameter, but the diameter may change over position, i.e. it may decrease or increase, as shown in particular in FIG. 3B to 3D. From such structural variations, a variation of the frictional force over the position may arise, as schematically shown in FIG. 4A to 4D.

Hence, for a particular syringe of a particular model, a particular batch, a particular volume and a particular brand a very specific dependence of the frictional force on the position may arise. Generally, the frictional force may be obtained from a statistical analysis by measuring different syringes of different types, models and volumes with respect to their friction as a function of position of the piston 21 relative to the tube 20 and, possibly, also as a function of the velocity by which the piston 21 is moved relative to the tube 20. From such statistical analysis for example a mean frictional force associated with a particular syringe (of a particular type, model, brand and volume) may be stored in the storage device 16. In addition, also the standard deviation of this mean frictional force may be stored for the particular syringe, the standard deviation indicating, as known from statistics, a possible deviation of a true frictional force from the stored mean frictional force.

Generally, if a particular syringe is used and if the true frictional force occurring between the piston 21 and the tube 20 is equal or at least close to the mean frictional force, the pressure value derived from the equation $$P = \frac{F - F_0}{S}.$$

will be (close to) 0 if no occlusion O is present, because it can be assumed that the measured force F is equal (or at least close) to the mean frictional force used as frictional force component F0 in the above equation. If however the true frictional force significantly deviates from the stored mean frictional force and if the stored mean frictional force is used in the above equation, the derived pressure value P deviates from the actual pressure P in the delivery line 3, which possibly may give rise to false alarms.

The likelihood for false alarms hence depends on the possible deviation of the true frictional force from the frictional force component used in the above equation. If in the above equation the stored mean frictional force (obtained for example from a statistical analysis of a multiplicity of syringes of a particular type, model, volume and brand) is used, the standard deviation expresses a possible deviation of a used syringe from the stored mean frictional force.

Hence, the stored standard deviation for a particular syringe (of a particular type, model, volume and brand) can be used to derive a second criteria, namely a second pressure threshold value candidate. For example, by multiplying the standard deviation by a constant factor, for example a factor of 2, a force error estimate may be derived, which then can be used to calculate the second threshold value candidate according to the following equation:

$$P_{thres,2}[\text{bar}] = \frac{F_{est}[gf]}{10.2 \cdot S[\text{mm}^2]}$$

Herein, $P_{thres,2}$ represents the second threshold value candidate (in bar), $F_{est}$ represents the force error estimate (in gram force (gf)) computed from for example the standard deviation (by multiplying the standard deviation by a constant factor), and S represents the effective cross sectional surface (in mm²) of the tube (20), defined as $S=\pi \cdot (D/2)^2$, D being the inner diameter of the cylindrical tube 20.

There are other possibilities to compute the force error estimate $F_{est}$. For example, the force error estimate may be computed by multiplying the mean frictional force stored in the storage device 16 by a constant factor, for example a factor of 1.5. Or the force error estimate may be stored directly as a parameter for different syringes of different types, models, volumes and brands within the storage device 16.

The actual pressure threshold $P_{thres}$ then is chosen as the maximum of the first threshold value candidate and the second threshold value candidate. In addition, limits may be defined, such that the pressure threshold value may not be lower than a lower limit (for example 50 mmHg) and not be higher than an upper limit (for example 900 mmHg).

Hence, by computing the two threshold value candidates and by determining the actual threshold value $P_{thres}$ from the two candidates, it can be obtained that a fast occlusion detection time is obtained, while at the same time keeping the likelihood for false alarms small.

The invention is not limited to the embodiments described above, but can be carried out in an entirely different fashion. In particular, the invention generally is applicable to different kinds of infusion devices used for different purposes for administering a medical fluid into a patient.

LIST OF REFERENCE NUMERALS

1 Infusion device
10 Housing
100 Front face
11 Pusher device
12 Receptacle
13 Display device
14 Force sensor
15 Processor device
16 Storage device
2 Pumping device (syringe)
20 Cylindrical tube
21 Piston
210 Piston head
211 Stopper
3 Delivery line
30, 31 End
A Actuation direction
B Patient
O Occlusion
P Pressure
$P_{thres}$ Pressure threshold
t time
T Duration

The invention claimed is:

1. An infusion device for administering a medical fluid to a patient, comprising:
   a receptacle for receiving a syringe having a tube containing a medical fluid and a piston movable with respect to the tube,
   a pusher device for acting onto the piston for pumping the medical fluid from the tube towards a patient,
   a sensor device for measuring a force acting in between the pusher device and the piston of the syringe, and
   a processor device for deriving, from the force measured by the sensor device, a pressure value indicative of a pressure in the tube, wherein the processor device is configured to compare the pressure value to a threshold value for determining whether an occlusion in a delivery line connected to the tube is present,
   wherein the processor device is configured to determine the threshold value from
   a first threshold value candidate computed based on a desired time between a time of an occurrence of an occlusion in the delivery line and a time at which the pressure value exceeds the threshold value, and
   a second threshold value candidate computed based on a force error estimate of a possible deviation between an expected frictional force and a true frictional force occurring when moving the piston relative to the tube.

2. The infusion device according to claim 1, wherein the threshold value is set to be the maximum of the first threshold value candidate and the second threshold value candidate.

3. The infusion device according to claim 1, further comprising a storage device storing a compliance value associated with the syringe and/or the delivery line connected to the tube of the syringe, wherein the processor device is configured to compute the first threshold value candidate from the stored compliance value, a set flow rate and the desired time.

4. The infusion device according to claim 3, wherein the processor device is configured to compute the first threshold value candidate according to the following equation:

$$P_{thres,1}[\text{bar}] = \frac{T_{desired}[\text{h}] \cdot f[\text{ml/h}]}{C[\text{ml/bar}]}$$

wherein
$P_{thres,1}$ represents the first threshold value candidate (in bar),
$T_{desired}$ represents the desired time (in hours) between the time of an occurrence of an occlusion in the delivery line and the time at which the pressure value exceeds the threshold value, C represents the compliance value (in ml/bar), and f represents the flow rate (in ml/h).

5. The infusion device according to claim 4, further comprising an input device allowing a user to program the flow rate and/or the desired time.

6. The infusion device according to claim 3, wherein the storage device stores a multiplicity of compliance values associated with a multiplicity of different syringes and/or delivery lines.

7. The infusion device according to claim 1, further compromising a storage device storing, for at least one particular syringe type, a mean frictional force required to move the piston relative to the tube and a standard deviation of the mean frictional force, wherein the processor device is configured to determine the force error estimate using the standard deviation for a syringe of a particular syringe type.

8. The infusion device according to claim 7, wherein the force error estimate is computed by multiplying the standard deviation by a constant factor.

9. The infusion device according to claim 7, wherein the stored mean frictional force and/or the stored standard deviation varies dependent on the position of the piston relative to the tube.

10. The infusion device according to claim 1, further comprising a storage device storing, for at least one particular syringe type, a mean frictional force required to move the piston relative to the tube, wherein the processor device is configured to determine the force error estimate by multiplying the mean frictional force by a constant factor.

11. The infusion device according to claim 1, further comprising a storage device storing, for different syringe types, parameter values indicating the force error estimate.

12. The infusion device according to claim 1, wherein the second threshold value candidate is computed according to the following equation:

$$P_{thres,2}[\text{bar}] = \frac{F_{est}[gf]}{10.2 \cdot S[\text{mm}^2]}$$

wherein $P_{thres,2}$ represents the second threshold value candidate (in bar), $F_{est}$ represents the force error estimate (in gram force (gf)), and S represents the effective cross sectional surface (in mm$^2$) of the tube, defined as $S=\pi \cdot (D/2)^2$, D being the inner diameter of the cylindrical tube.

13. A method for administering a medical fluid to a patient using an infusion device, comprising:

receiving a syringe having a tube containing a medical fluid and a piston movable with respect to the tube in a receptacle of the infusion device, pumping the medical fluid from the tube towards a patient by acting onto the piston using a pusher device, measuring a force acting in between the pusher device and the piston of the syringe using a sensor device, and deriving, from the force measured by the sensor device, a pressure value indicative of a pressure in the tube of the syringe using a processor device, wherein the pressure value is compared to a threshold value for determining whether an occlusion in a delivery line connected to the tube is present, wherein the threshold value is determined from a first threshold value candidate computed based on a desired time between a time of an occurrence of an occlusion in the delivery line and a time at which the pressure value exceeds the threshold value, and a second threshold value candidate computed based on a force error estimate of a possible deviation between an expected frictional force and a true frictional force occurring when moving the piston relative to the tube.

* * * * *